(12) United States Patent
Xie et al.

(10) Patent No.: US 10,973,867 B2
(45) Date of Patent: Apr. 13, 2021

(54) COMPOSITIONS AND METHODS FOR TREATING RETINOPATHY

(71) Applicant: Marshall University Research Corporation, Huntington, WV (US)

(72) Inventors: Zijian Xie, Huntington, WV (US); Joseph I. Shapiro, Huntington, WV (US)

(73) Assignee: MARSHALL UNIVERSITY RESEARCH CORPORATION, Huntington, WV (US)

( * ) Notice: Subject to any disclaimer, the term of this patent is extended or adjusted under 35 U.S.C. 154(b) by 13 days.

(21) Appl. No.: 16/067,483

(22) PCT Filed: Dec. 30, 2016

(86) PCT No.: PCT/US2016/069451
§ 371 (c)(1),
(2) Date: Jun. 29, 2018

(87) PCT Pub. No.: WO2017/117512
PCT Pub. Date: Jul. 6, 2017

(65) Prior Publication Data
US 2020/0030404 A1 Jan. 30, 2020

Related U.S. Application Data

(60) Provisional application No. 62/273,224, filed on Dec. 30, 2015.

(51) Int. Cl.
| | | |
|---|---|---|
| *A61K 38/10* | (2006.01) | |
| *A61K 38/16* | (2006.01) | |
| *A61K 38/46* | (2006.01) | |
| *C07K 14/00* | (2006.01) | |
| *A61P 9/10* | (2006.01) | |
| *A61K 38/00* | (2006.01) | |
| *A61K 9/00* | (2006.01) | |

(52) U.S. Cl.
CPC .......... *A61K 38/005* (2013.01); *A61K 9/0048* (2013.01); *A61K 38/10* (2013.01); *A61K 38/162* (2013.01); *A61K 38/46* (2013.01); *A61P 9/10* (2018.01); *C12Y 306/03009* (2013.01)

(58) Field of Classification Search
CPC ...... A61K 38/005; A61K 38/10; A61K 38/16; A61K 38/162; A61K 38/46; A61K 47/645; A61K 9/0048; C07K 14/00; C07K 2319/10; A61P 9/10; C12Y 306/03009
USPC ...... 514/21.4, 1.1, 17.4, 21.3; 530/300, 325, 530/324, 326
See application file for complete search history.

(56) References Cited

U.S. PATENT DOCUMENTS

| | | | |
|---|---|---|---|
| 6,440,933 | B1 | 8/2002 | Bodor et al. |
| 6,777,534 | B1 | 8/2004 | Klagsbrun et al. |
| 7,888,059 | B2 | 2/2011 | Karlish et al. |
| 8,283,441 | B2 | 10/2012 | Xie et al. |
| 8,329,866 | B2 | 12/2012 | Rosendahl et al. |
| 8,372,811 | B2 | 2/2013 | Jang et al. |
| 8,470,784 | B2 | 6/2013 | Liu et al. |
| 2008/0268051 | A1 | 10/2008 | Hughes et al. |
| 2010/0068198 | A1 | 3/2010 | Mijatovic et al. |
| 2010/0093624 | A1 | 4/2010 | Low et al. |
| 2014/0141002 | A1* | 5/2014 | Clemmons .............. A61P 43/00 424/139.1 |
| 2014/0154264 | A1 | 6/2014 | Cheresh et al. |
| 2014/0187484 | A1 | 7/2014 | Xie et al. |
| 2015/0045296 | A1 | 2/2015 | Bhattacharjee |

FOREIGN PATENT DOCUMENTS

| | | |
|---|---|---|
| WO | 2006/044916 A2 | 4/2006 |
| WO | 2013/169931 A2 | 11/2013 |
| WO | 2014/033184 A1 | 3/2014 |
| WO | 2014/075137 A1 | 5/2014 |
| WO | 2014/131815 A1 | 9/2014 |
| WO | 2015/004626 A2 | 1/2015 |
| WO | 2015/130783 A1 | 9/2015 |

OTHER PUBLICATIONS

European Patent Office, Extended European Search Report issued in corresponding Application No. 16882743.4 dated Jun. 7, 2019.
Wang, Y., et al. "Involvement of Na/K-ATPase in hydrogen peroxide-induced activiation of the Src/ERK pathway in LLC-PK1 cells." Free Radical Biology and Medicine 71 (2014) 415-426.
Yan, Y., et al. "Involvement of Reactive Oxygen Species in a Feed-forward Mechanism of Na/K-ATPase-mediated Signaling Transduction." Journal of Biological Chemistry, vol. 288, No. 47 (2013) 34249-34258.
Liu, J., et al. "Attenuation of Na/K-ATPase Mediated Oxidant Amplification with pNaKtide Ameliorates Experimental Uremic Cardiomyopathy." Scientific Reports (2016) 6:34592, DOI: 10.1038/srep34592.
Sodhi, K., et al. "pNaKtide inhibits Na/K-ATPase reactive oxygen species amplification and attenuates adipogenesis." Sci. Adv. (2015), 1:31500781.
Sodhi, K., et al. "pNaKtide Attenuates Steatohepatitis and Atherosclerosis by Blocking Na/K-ATPase/ROS Amplification in C57BI6 and ApoE Knockout Mice Fed a Western Diet." Scientific Reports (2016), 7:193, DOI:10.1038/s41598-017-00306-5.

(Continued)

*Primary Examiner* — Julie Ha
(74) *Attorney, Agent, or Firm* — Stites & Harbison, PLLC; Terry L. Wright

(57) ABSTRACT

Methods for treating retinopathy are provided and include administering an effective amount of a polypeptide antagovist of a Na/K ATPase/Src receptor complex to a subject. The retinopathy can include diabetic retinopathy. Methods of decreasing angiogenesis in a retinal vasculature are also provided and include the step of administering, such as by intravitreous injection, a polypeptide antagonist of a Na/K ATPase/Src receptor complex to a subject in need thereof.

10 Claims, 8 Drawing Sheets
Specification includes a Sequence Listing.

(56) References Cited

OTHER PUBLICATIONS

Li, S., et al. "NaKtide, a Na/K-ATPase-derived Peptide Src Inhibitor, Antagonizes Ouabain-activated Signal Transduction in Cultured Cells." Journal of Biological Chemistry, vol. 284, No. 31 (2009), 21066-21076.

Li, Z., et al. "Na/K-ATPase Mimetic pNaKtide Peptide Inhibits the Growth of Human Cancer Cells." Journal of Biological Chemistry, vol. 286, No. 37 (2011), 32394-32403.

United States Patent and Trademark Office, International Search Report and Written Opinion issued in corresponding Application No. PCT/US16/69451, dated Jul. 3, 2017.

Kollias, A., et al. "Diabetic Retinopathy Early Diagnosis and Effective Treatment." Deutches Arzteblatt International (2010) vol. 107, 75-84, DOI: 10.3238/arztebl.2010.0075.

* cited by examiner

A

B

SEQUENCE LISTING

```
<160> NUMBER OF SEQ ID NOS: 5

<210> SEQ ID NO 1
<211> LENGTH: 20
<212> TYPE: PRT
<213> ORGANISM: Homo sapiens

<400> SEQUENCE: 1

Ser Ala Thr Trp Leu Ala Leu Ser Arg Ile Ala Gly Leu Cys Asn Arg
1               5                   10                  15

Ala Val Phe Gln
            20

<210> SEQ ID NO 2
<211> LENGTH: 13
<212> TYPE: PRT
<213> ORGANISM: Human immunodeficiency virus

<400> SEQUENCE: 2

Gly Arg Lys Lys Arg Arg Gln Arg Arg Arg Pro Pro Gln
1               5                   10

<210> SEQ ID NO 3
<211> LENGTH: 16
<212> TYPE: PRT
<213> ORGANISM: Drosophila melanogaster
```

```
<400> SEQUENCE: 3

Arg Gln Ile Lys Ile Trp Phe Gln Asn Arg Arg Met Lys Trp Lys Lys
1               5                   10                  15

<210> SEQ ID NO 4
<211> LENGTH: 8
<212> TYPE: PRT
<213> ORGANISM: Homo sapiens

<400> SEQUENCE: 4

Lys Lys Gly Lys Lys Gly Lys Lys
1               5

<210> SEQ ID NO 5
<211> LENGTH: 33
<212> TYPE: PRT
<213> ORGANISM: Artificial Sequence
<220> FEATURE:
<223> OTHER INFORMATION: TAT NaKtide Fusion Polypeptide

<400> SEQUENCE: 5

Gly Arg Lys Lys Arg Arg Gln Arg Arg Pro Pro Gln Ser Ala Thr
1               5                   10                  15

Trp Leu Ala Leu Ser Arg Ile Ala Gly Leu Cys Asn Arg Ala Val Phe
            20                  25                  30

Gln
```

COMPOSITIONS AND METHODS FOR TREATING RETINOPATHY

RELATED APPLICATION

This application claims priority from U.S. Provisional Application Ser. No. 62/273,224, filed Dec. 30, 2015, the entire disclosure of which is incorporated herein by this reference.

GOVERNMENT INTEREST

This invention was made with government support under grant number HL 109015 awarded by the National Institutes of Health. The government has certain rights in the invention.

TECHNICAL FIELD

The presently-disclosed subject matter relates to compositions and methods for treating retinopathy and/or decreasing angiogenesis in a retinal vasculature. In particular, the presently-disclosed subject matter relate to polypeptides and methods for using the polypeptides to treat retinopathy and/or decrease angiogenesis in a retinal vasculature.

BACKGROUND

The Na/K-ATPase enzyme is ubiquitously expressed in most eukaryotic cells and helps maintains the trans-membrane ion gradient by pumping $Na^+$ out and $K^+$ into cells. The Na/K-ATPase interacts directly with Src via at least two binding motifs: one being between the CD2 of the α1 subunit and Src SH2; and, the other involving the third cytosolic domain (CD3) and Src kinase domain. The formation of this Na/K-ATPase and Src complex serves as a receptor for ouabain to provoke protein kinase cascades. Specifically, binding of ouabain to Na/K-ATPase will disrupt the latter interaction, and then result in assembly and activation of different pathways including ERK cascades, PLC/PKC pathway and ROS production. Moreover, this interaction keeps Src in an inactive state. Thus, the Na/K-ATPase functions as an endogenous negative Src regulator. See also International Patent Application Nos. WO 2008/054792 and WO 2010/071767, which are both incorporated herein by reference.

Src family kinases are 52-62-kDa membrane-associated nonreceptor tyrosine kinases and they participate in several tyrosine phosphorylation-related signaling pathways in response to various extracellular ligands. Src, for example, contains at least three protein interaction domains. The SH3 domain binds to polyproline motifs and the SH2 domain interacts with the phosphorylated tyrosine residues. The kinase domain reacts with the nucleotide and phosphorylates the substrate. Binding of protein ligands to the SH3 or SH2 domain can activate Src. Proteins that bind with kinase domain of Src were also reported to be capable of regulating Src activity.

It is further appreciated that the Na+/K+-ATPase interacts with Src and Src family kinases to form a functional receptor. Binding of ouabain to this receptor activates Src, which in turn phosphorylates various effectors, resulting in the assembly and activation of different pathways including the Ras/Raf/ERK1/2 and phospholipase C/protein kinase C cascades as well as increases in intracellular $Ca^{2+}$ and cellular ROS production. The activation of these signaling pathways eventually leads to changes in cardiac and renal functions, stimulation of cell proliferation and tissue fibrosis, protection of tissue against ischemia/reperfusion injury, inhibition of cancer cell growth, and more. Src and ROS are also involved in the induction of VEGF expression. While many known Src and Src family kinase inhibitors are developed as ATP analogs that compete for ATP binding to these kinases, such Src inhibitors lack pathway specificity.

Additionally, many types of retinopathy are proliferative, most often resulting from neovascularization or blood vessel overgrowth. Angiogenesis is a precursor in retinopathy that may result in blindness or severe vision loss. Diabetic retinopathy (DR) is a complication of diabetes, and the leading cause of blindness among working age adults in developed countries. There were more than 371 million diabetic patients worldwide in 2012, and the number is increasing rapidly. The disease is initiated by high glucose-induced vascular dysfunction and remodeling. This is followed by tissue ischemia/hypoxia and subsequent angiogenesis (neovascularization) because of increased production of VEGF and other growth factors, leading to proliferative diabetic retinopathy (PDR). Moreover, under the pathological conditions of diabetic retinopathy, the increase in ROS and the activation of Src are keys to VEGF-mediated endothelial cell proliferation and vessel leakage that are the pathological basis of diabetic neovascularization. DR can further develop to fibrovascular proliferation on the surface of the retina due to tissue fibrosis, causing retinal detachment.

Despite considerable advances in the management of DR, complications of various therapies have brought the requirement for novel modalities in treating DR. Previous studies have shown the significant role of VEGF in ocular neovascularization. Levels of ocular VEGF are elevated in both animal models and PDR patients. Furthermore, injection of VEGF into normal primate eyes induces pathological processes similar to those seen in DR, including microaneurysm formation and increased vascular permeability. Because VEGF has been shown to play a major role in retinal neovascularization, anti-VEGF treatments have been developed for DR. Over the past 10 years, several anti-VEGF drugs have been developed and used in PDR patients.

Many clinical studies have demonstrated the benefits with intravitreal injection of anti-VEGF drugs for PDR. However, many important issues remain. First, anti-VEGF therapy does not address the underlying cause of the problem (i.e., high glucose and continued vascular remodeling/fibrosis because of uncontrolled diabetes in these patients). Second, clinical problems with anti-VEGF therapy have been noted partly because of the use of anti-VEGF antibody. Some of the observed side effects include increased cataract formation, vitreous hemorrhage, tractional retinal detachment, elevated intraocular pressure, infection and macular hole. Moreover, there is evidence that some of the injected anti-VEGF antibodies are detected in systemic circulation, which could produce more severe systemic side effects. Thus, there is currently an unmet need in care for patients with diabetic retinopathy and, in particular, there remains a need for compositions and methods for treating diabetic retinopathy.

SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this summary does not list or suggest all possible combinations of such features.

The presently-disclosed subject matter includes compositions and methods for treating retinopathy and/or decreasing angiogenesis in a retinal vasculature. In particular, the presently-disclosed subject matter includes methods for treating retinopathies and/or decreasing angiogenesis in a retinal vasculature with a polypeptide. In some embodiments, the retinopathy is diabetic retinopathy. In some embodiments, the polypeptide is used to treat a retinopathy and/or decrease angiogenesis in a retinal vasculature by inhibiting the receptor function of the Na/K-ATPase and Src complex, and, in some embodiments, the polypeptide inhibits the receptor function by acting as an antagonist of the Na/K-ATPase and Src complex.

In some embodiments, a method for treating a retinopathy and/or decreasing angiogenesis in a retinal vasculature is provided that includes administering an effective amount of polypeptide antagonist of a Na/K ATPase/Src receptor complex to a subject in need thereof. In some embodiments, the polypeptide antagonist comprises the sequence of SEQ ID NO: 1, or a fragment, and/or variant thereof. In some embodiments, the polypeptide antagonist further includes a cell penetrating polypeptide encoded by an amino acid sequence selected from the group consisting of SEQ ID NOS: 2-4. In some embodiments, administering the polypeptide includes intravitreous administration, subconjunctival administration, intracameral administration, intraocular administration, or combinations thereof.

With further respect to the administration of the polypeptide antagonist described for use herein, in some embodiments, administering the polypeptide antagonist (e.g., the polypeptide of SEQ ID NO: 1) reduces one or more symptoms and/or characteristics associated with retinopathy. For example, in some embodiments, administering the polypeptide antagonist decreases cell proliferation in an eye of a subject. In some embodiments, administering the polypeptide antagonist decreases vascular endothelial growth factor (VEGF) expression, angiogenesis, and/or capillary tube formation in the eye of the subject. Further, in some embodiments, administering the polypeptide antagonist decreases neovascularization in the eye of the subject.

Further features and advantages of the present invention will become evident to those of ordinary skill in the art after a study of the description, figures, and non-limiting examples in this document.

BRIEF DESCRIPTION OF THE DRAWINGS

FIG. 2B is a graph showing quantitative data from the matrigel assays generated via Image J. Values are mean±SEM, and * indicates p<0.05. Each sample was tested in duplicate, and the Matrigel assay was performed 3 independent times.

FIG. 3A shows the Western blot results of expression of VEGF in tumor homogenates treated with either saline or pNaKtide. Quantitative results of the study are shown in the graph, and show that pNaKtide treatment produced a greater than 50% reduction in total VEGF. *, p<0.05; **, p<0.01. FIG. 3B includes results of the investigation of effects of pNaKtide on angiogenesis. Images of the vessel density of xenograft tumors was evaluated by IHC staining of CD31 in the formalin-fixed, paraffin-embedded xenograft tumors (14 in saline group and 6 in 10 mg/kg pNaKtide group). The graph provides the quantitative results of vessel density calculated as the percent of tumor area occupied by vessels.

FIG. 4 is an image of the retinal vasculature of a normal control, which remained in room air (scale bar=100 µm). FIG. 5 includes an image of the retinal vasculature of an OIR mouse in a study of pNaKtide on neovascularization (scale bar=100 µm). FIG. 6 includes an image of the retinal vasculature showing the effects of intravitreous injection of 1 µl of pNaKtide (0.25 µg/µl) (scale bar=100 µm) on the OIR mouse model. FIG. 7 includes a quantitative graph of retinal vaso-obliteration in OIR as percent of total retinal area. Data are presented as mean±SEM, statistical differences were assessed using the 2-tailed Student's t test, and p values less than 0.05 were considered significant  p<0.01. FIG. 8 includes a quantitative graph of retinal neovascularization in OIR as percent of total retinal area. Data are presented as mean±SEM, statistical differences were assessed using the 2-tailed Student's t test, and p values less than 0.05 were considered significant  p<0.01.

BRIEF DESCRIPTION OF THE SEQUENCE LISTING

Figure 1:
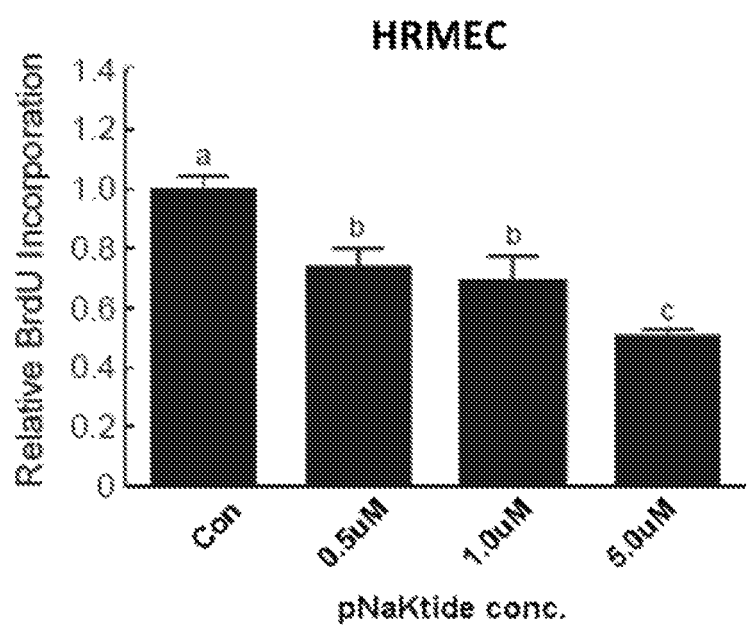
FIG. 1 includes a graph showing the effect of increasing concentrations of a polypeptide antagonist of a Na/K ATPase/Src receptor of the presently-disclosed subject matter (pNaKtide) on the proliferation of human retinal microvascular endothelial cells (HRMECs) over a twenty-four hour period. Proliferation of the cells was measured by a bromodeoxyuridine (BrdU) assay. Each sample was tested in duplicate, and the BrdU assay was performed 3 independent times. Values are mean±SEM, and b and c indicate p<0.05, and p<0.01 vs control, respectively.

SEQ ID NO: 1 is an amino acid sequence encoding an embodiment of a polypeptide in accordance with the presently-disclosed subject matter (NaKtide);

SEQ ID NO: 2 is an amino acid sequence encoding a TAT cell penetrating peptide;

SEQ ID NO: 3 is an amino acid sequence encoding a penetratin (AP) cell penetrating peptide; and SEQ ID NO: 4 is an amino acid sequence encoding the N-terminal poly-lysine domain of the a1 subunit of Na/K-ATPase (A1N).

SEQ ID NO: 5 is another amino acid sequence of an embodiment of a polypeptide in accordance with the presently-disclosed subject matte (pNaKtide).

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding, and no unnecessary limitations are to be understood therefrom.

The presently-disclosed subject matter includes compositions and methods for treating retinopathy and/or decreasing angiogenesis in a retinal vasculature. In particular, the presently-disclosed subject matter includes polypeptides and methods for using the polypeptides to treat retinopathy and/or decrease angiogenesis in a retinal vasculature.

The term "retinopathy" as used herein includes ocular manifestations of systemic disease as seen in diabetes, arterial hypertension, retinal vein or artery occlusion, sickle cell disease or arterial hypertension as well as retinopathy of prematurity (ROP), radiation retinopathy, sickle cell disease. In some instances, and as described in further detail below, such retinopathy can be characterized by one or more levels of angiogenic capillary tube formation, blood vessel formation, cell proliferation, vascular endothelial growth factor (VEGF) expression, and combinations thereof.

In some embodiments of the presently-disclosed subject matter, the polypeptide utilized to treat retinopathy and/or decrease angiogenesis in a retinal vasculature of a subject inhibits the receptor function of the Na/K-ATPase and Src complex. In some embodiments, the polypeptide is an antagonist for the receptor function of the Na/K-ATPase and Src complex. In some embodiments, the polypeptides are comprised of the sequence of SEQ ID NO: 1 (NaKtide), or fragments, and/or variants thereof.

The terms "polypeptide," "protein," and "peptide" are used interchangeably herein to refer to a polymer of the protein amino acids regardless of its size or function. The terms "protein," "polypeptide," and "peptide" are used interchangeably herein to also refer to a gene product, homologs, orthologs, paralogs, fragments, any protease derived peptide (fragment), and other equivalents, variants, and analogs of a polymer of amino acids. The terms "polypeptide fragment" or "fragment" when used in reference to such a reference polypeptide, refer to a polypeptide in which amino acid residues are deleted as compared to the reference polypeptide itself, but where the remaining amino acid sequence is usually identical to the corresponding positions in the reference polypeptide. Such deletions may occur at the amino-terminus of the reference polypeptide, the carboxy-terminus of the reference polypeptide, or both. Polypeptide fragments can also be inclusive of "functional fragments," in which case the fragment retains some or all of the activity of the reference polypeptide.

The term "variant," as used herein, refers to an amino acid sequence that is different from the reference polypeptide by one or more amino acids. In some embodiments, a variant polypeptide may differ from a reference polypeptide by one or more amino acid substitutions. For example, a NaKtide polypeptide variant can differ from the NaKtide polypeptide of SEQ ID NO: 1 by one or more amino acid substitutions, i.e., mutations. In this regard, polypeptide variants comprising combinations of two or more mutations can respectively be referred to as double mutants, triple mutants, and so forth. It will be recognized that certain mutations can result in a notable change in function of a polypeptide, while other mutations will result in little to no notable change in function of the polypeptide.

In some embodiments, the present polypeptides include polypeptides that share at least 75% homology with the pNaKtide polypeptide of SEQ ID NO: 1. In some embodiments, the polypeptides share at least 85% homology with the NaKtide polypeptide of SEQ ID NO: 1. In some embodiments, the polypeptides share at least 90% homology with the NaKtide polypeptide of SEQ ID NO: 1. In some embodiments, the polypeptides share at least 95% homology with the NaKtide polypeptide of SEQ ID NO: 1.

"Percent identity," or "percent homology" when used herein to describe to an amino acid sequence or a nucleic acid sequence, relative to a reference sequence, can be determined using the formula described by Karlin and Altschul (Proc. Natl. Acad. Sci. USA 87: 2264-2268, 1990, modified as in Proc. Natl. Acad. Sci. USA 90:5873-5877, 1993). Such a formula is incorporated into the basic local alignment search tool (BLAST) programs of Altschul et al. (J. Mol. Biol. 215: 403-410, 1990).

In some embodiments of the presently-disclosed polypeptides, the polypeptides further comprise one or more leader sequences and, in some embodiments, leader sequences including, but not limited to, cell penetrating peptides (CPPs). The term "cell penetrating peptide" (CPP) is used herein to generally refer to short peptides that facilitate the transport of molecular cargo across plasma membranes found in a cell. In some instances, the molecular cargo includes another polypeptide, such as the polypeptides described herein. Of course, the cell penetrating peptides can be conjugated to the molecular cargo (e.g., polypeptide) via any number of means, including covalent bonds and/or non-covalent bonds. In a number of instances, however, such cell penetrating peptides will often include a relatively high concentration of positively-charged amino acids, such as lysine and arginine, and will have a sequence that contains an alternating pattern of charged (polar) and non-charged amino acids.

In some embodiments of the presently-disclosed subject matter, an exemplary leader sequence or cell-penetrating peptide can include the trans-activating transcriptional activator (TAT) cell penetrating peptide, which is represented by the sequence of SEQ ID NO: 2 (GRKKRRQRRRPPQ). Another exemplary leader sequence includes penetratin (AP), which is represented by the sequence of SEQ ID NO: 3 (RQIKIWFQNRRMKWKK). Yet another exemplary leader sequence includes an amino acid sequence encoding the N-terminal poly-lysine domain of the al subunit of Na/K-ATPase (AlN), which is represented by the sequence of SEQ ID NO: 4 (KKGKKGKK). Those of ordinary skill will appreciate though that other leader sequences, including other cell penetrating peptides, can also be used in conjunction with the presently-disclosed polypeptides. In some embodiments, a polypeptide including a leader sequence, such as a cell penetrating peptide, attached to the NaKtide sequence of SEQ ID NO: 1 is referred to herein as a pNaKtide (e.g., SEQ ID NO: 5; GRKKRRQRRRPPQSATWLALSRIAGLCNRAVFQ, which includes the TAT cell penetrating peptide of SEQ ID NO: 2 fused to the NaKtide sequence of SEQ ID NO: 1).

The presently-disclosed subject matter further includes and makes use of pharmaceutical compositions comprising the polypeptides described herein along with a pharmaceutically-acceptable carrier. Indeed, when referring to certain embodiments herein, the terms "polypeptide" and/or "composition" may or may not be used to refer to a pharmaceutical composition that includes the polypeptide.

The term "pharmaceutically-acceptable carrier" as used herein refers to sterile aqueous or nonaqueous solutions, dispersions, suspensions, or emulsions, as well as sterile powders for reconstitution into sterile injectable solutions or dispersions just prior to use. Proper fluidity can be maintained, for example, by the use of coating materials such as lecithin, by the maintenance of the required particle size in the case of dispersions and by the use of surfactants. These compositions can also contain adjuvants, such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like.

Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of polypeptide to biodegradable polymer and the nature of the particular biodegradable polymer employed, the rate of polypeptide release can be controlled. Depot injectable formulations can also be prepared by entrapping the polypeptide in liposomes or microemulsions, which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose.

Suitable formulations can further include aqueous and non-aqueous sterile injection solutions that can contain antioxidants, buffers, bacteriostats, bactericidal antibiotics, and solutes that render the formulation isotonic with the bodily fluids of the intended recipient; and aqueous and non-aqueous sterile suspensions, which can include suspending agents and thickening agents.

The compositions can also take forms such as suspensions, solutions, or emulsions in oily or aqueous vehicles, and can contain formulatory agents such as suspending, stabilizing and/or dispersing agents. Alternatively, the polypeptides can be in powder form for constitution with a suitable vehicle, e.g., sterile pyrogen-free water, before use.

The formulations can be presented in unit-dose or multi-dose containers, for example sealed ampoules and vials, and can be stored in a frozen or freeze-dried (lyophilized) condition requiring only the addition of sterile liquid carrier immediately prior to use.

For oral administration, the compositions can take the form of, for example, tablets or capsules prepared by a conventional technique with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycollate); or wetting agents (e.g., sodium lauryl sulphate). The tablets can be coated by methods known in the art.

Liquid preparations for oral administration can take the form of, for example, solutions, syrups or suspensions, or they can be presented as a dry product for constitution with water or other suitable vehicle before use. Such liquid preparations can be prepared by conventional techniques with pharmaceutically acceptable additives such as suspending agents (e.g., sorbitol syrup, cellulose derivatives or hydrogenated edible fats); emulsifying agents (e.g. lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound. For buccal administration, the compositions can take the form of tablets or lozenges formulated in a conventional manner.

The compositions can also be formulated as a preparation for implantation or injection. Thus, for example, the compounds can be formulated with suitable polymeric or hydrophobic materials (e.g., as an emulsion in an acceptable oil) or ion exchange resins, or as sparingly soluble derivatives (e.g., as a sparingly soluble salt). The compounds can also be formulated in rectal compositions, creams or lotions, or transdermal patches.

As described herein, the presently-disclosed subject matter further includes methods for treating retinopathies with a polypeptide. Some embodiments of methods include administering one of the presently-disclosed polypeptides to a subject in need thereof. The polypeptide can treat a retinopathy by inhibiting the receptor function of the Na/K-ATPase and Src complex and, in some embodiments, the polypeptides inhibit the receptor function by acting as an antagonist of the Na/K-ATPase and Src complex.

The term "inhibiting" or "inhibition" does not necessarily refer to the ability to completely inactivate all target biological activity in all cases. Rather, the skilled artisan will understand that the term "inhibiting" can be used, in some instances, interchangeably with the term "decreasing" and refers to decreasing biological activity of a target, such as can occur when a ligand binds a site of the target, a protein in a biochemical pathway of the target is blocked, a non-native complexes with a target, or the like. Such decrease in biological activity can be determined relative to a control, wherein the control can be representative of an environment in which an inhibitor is not administered. For example, in some embodiments, a decrease in activity relative to a control can be about a 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% decrease.

With further regard to the treatment of a retinopathy, the terms "treatment" or "treating" refer to the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another therapy directed toward the improvement of the associated disease, pathological condition, or disorder.

The treatment of a retinopathy can be measured and quantified in several different ways. In some embodiments, treatment of a retinopathy can be measured and quantified by, among other things, blood vessel formation and VEGF expression, or a combination thereof. Alternatively or additionally, treatment of a retinopathy can be characterized by angiogenic capillary tube formation. Treatment of a retinopathy can also be characterized by a decrease in angiogenesis, in other instances, decreased and/or inhibited VEGF expression, a decrease in cell proliferation, and combinations thereof. In some embodiments, the increases and/or decreases described herein can be in reference to a control subject having a retinopathy and that has not been treated with one of the presently-disclosed polypeptides. In other embodiments, the increases and/or decreases described herein can be in reference to a baseline measurement of the subject prior to treatment with one of the presently-disclosed polypeptides. Such characteristics or symptoms of retinopathy can be measured by any number of methods known to those of ordinary skill in the art.

In some embodiments of the presently-disclosed subject matter, the administration of a polypeptide describe herein need not treat, inhibit, and/or decrease every symptom or characteristic of a retinopathy. For instance, in some embodiments of the presently-disclosed subject matter, the administration of a polypeptide reduces an amount of angiogenesis, or new blood vessel formation, in the retinal vasculature of a subject. As such, in some embodiments, a method of reducing angiogenesis in a retinal vasculature is also provided that comprises administering a polypeptide antagonist of a NaK ATPase/Src receptor complex to a subject in need thereof. In some embodiments, the polypeptide anatagonist comprises the sequence of SEQ ID NO: 1, or a fragment, and/or variant thereof. In some embodiments, the polypeptide anatagonist further includes a cell penetrating polypeptide encoded by an amino acid sequence selected from the group consisting of SEQ ID NOS: 2-4.

For administration of a therapeutic composition as disclosed herein (e.g., a polypeptide antagonist comprising the sequence of SEQ ID NO: 5), conventional methods of extrapolating human dosage based on doses administered to a murine animal model can be carried out using the conversion factor for converting the mouse dosage to human dosage: Dose Human per kg=Dose Mouse per kg/12 (Freireich, et al., (1966) Cancer Chemother Rep. 50: 219-244). Doses can also be given in milligrams per square meter of body surface area because this method rather than body weight achieves a good correlation to certain metabolic and excretionary functions. Moreover, body surface area can be used as a common denominator for drug dosage in adults and children as well as in different animal species as described by Freireich, et al. (Freireich et al., (1966) Cancer Chemother Rep. 50:219-244). Briefly, to express a mg/kg dose in any given species as the equivalent mg/sq m dose, multiply the dose by the appropriate km factor. In an adult human, 100 mg/kg is equivalent to 100 mg/kg×37 kg/sq m=3700 mg/m².

Suitable methods for administering a therapeutic composition in accordance with the methods of the presently-disclosed subject matter include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, subcutaneous administration, intravitreous administration, intracameral (into anterior chamber) administration, subretinal administration, sub-Tenon's administration, peribulbar administration, administration via topical eye drops, and the like. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

In some embodiments, and for ocular formulations, routes of administration include, but are not limited to, topical ocular administration, subconjunctival injections, intracameral injections, intravitreal injections, and intraocular implants. Ocular bioavailability after topical eye drop administration, the most common and least traumatic form of ocular medication, is low and is often used for diseases of the anterior segment of the eye. Blood-ocular barriers, including tight junctional complexes between ciliary and retinal pigmented epithelium, are defense mechanisms to protect the eye. Unfortunately, they also act as a considerable barrier to systemically administered drugs, but subconjunctival, intracameral and intravitreal injections can deliver drugs to the anterior and posterior chambers of the eye. For ocular applications then, in some instances, a pNaKtide can be applied to the vitreous body by topic eye drop instillation, or subconjunctival, intracameral or intravitreal injections, or by intraocular implants.

Regardless of the route of administration, the compositions of the presently-disclosed subject matter are typically administered in amount effective to achieve the desired response. As such, the term "effective amount" is used herein to refer to an amount of the therapeutic composition (e.g., a pNaKtide) sufficient to produce a measurable biological response (e.g., a decrease in retinopathy or angiogenesis). Actual dosage levels of active ingredients in a therapeutic composition of the present invention can be varied so as to administer an amount of the active compound(s) that is effective to achieve the desired therapeutic response for a particular subject and/or application. Of course, the effective amount in any particular case will depend upon a variety of factors including the activity of the therapeutic composition, formulation, the route of administration, combination with other drugs or treatments, severity of the condition being treated, and the physical condition and prior medical history of the subject being treated. Preferably, a minimal dose is administered, and the dose is escalated in the absence of dose-limiting toxicity to a minimally effective amount. Determination and adjustment of a therapeutically effective dose, as well as evaluation of when and how to make such adjustments, are known to those of ordinary skill in the art.

For additional guidance regarding formulation and dose, see U.S. Pat. Nos. 5,326,902; 5,234,933; PCT International Publication No. WO 93/25521; Berkow et al., (1997) The Merck Manual of Medical Information, Home ed. Merck Research Laboratories, Whitehouse Station, N.J.; Goodman et al., (1996) Goodman & Gilman's the Pharmacological Basis of Therapeutics, 9th ed. McGraw-Hill Health Professions Division, New York; Ebadi, (1998) CRC Desk Reference of Clinical Pharmacology. CRC Press, Boca Raton, Fla.; Katzung, (2001) Basic & Clinical Pharmacology, 8th ed. Lange Medical Books/McGraw-Hill Medical Pub. Division, New York; Remington et al., (1975) Remington's Pharmaceutical Sciences, 15th ed. Mack Pub. Co., Easton, Pa.; and Speight et al., (1997) Avery's Drug Treatment: A Guide to the Properties, Choice, Therapeutic Use and Economic Value of Drugs in Disease Management, 4th ed. Adis International, Auckland/Philadelphia; Duch et al., (1998) Toxicol. Lett. 100-101:255-263.

As used herein, the term "subject" includes both human and animal subjects. Thus, veterinary therapeutic uses are provided in accordance with the presently disclosed subject matter. As such, the presently-disclosed subject matter provides for the treatment of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

The practice of the presently-disclosed subject matter can employ, unless otherwise indicated, conventional techniques of cell biology, cell culture, molecular biology, transgenic biology, microbiology, recombinant DNA, and immunology, which are within the skill of the art. Such techniques are explained fully in the literature. See e.g., Molecular Cloning A Laboratory Manual (1989), 2nd Ed., ed. by Sambrook, Fritsch and Maniatis, eds., Cold Spring Harbor Laboratory Press, Chapters 16 and 17; U.S. Pat. No. 4,683,195; DNA Cloning, Volumes I and II, Glover, ed., 1985; Oligonucleotide Synthesis, M. J. Gait, ed., 1984; Nucleic Acid Hybridization, D. Hames & S. J. Higgins, eds., 1984; Transcription and Translation, B. D. Hames & S. J. Higgins, eds., 1984; Culture Of Animal Cells, R. I. Freshney, Alan R. Liss, Inc., 1987; Immobilized Cells And Enzymes, IRL Press, 1986; Perbal (1984), A Practical Guide To Molecular Cloning; See Methods In Enzymology (Academic Press, Inc., N.Y.); Gene Transfer Vectors For Mammalian Cells, J. H. Miller and M. P. Calos, eds., Cold Spring Harbor Laboratory, 1987; Methods In Enzymology, Vols. 154 and 155, Wu et al., eds., Academic Press Inc., N.Y.; Immunochemical Methods In Cell And Molecular Biology (Mayer and Walker, eds., Academic Press, London, 1987; Handbook Of Experimental Immunology, Volumes I-IV, D. M. Weir and C. C. Blackwell, eds., 1986.

The presently-disclosed subject matter is further illustrated by the following specific but non-limiting examples. The examples may include compilations of data that are representative of data gathered at various times during the course of development and experimentation related to the presently-disclosed subject matter.

EXAMPLES

Materials and Methods for Examples 1-4

Effect of pNaKtide on Cell Proliferation.

To measure the effect of increased pNaKtide on HRMECs, cells were incubated with bromodeoxyuridine (BrdU), a nucleotide analog that is incorporated during S-phase in the DNA of proliferating cells. After overnight incubation, the cells were treated with 0.1 µM, 1 µM, and 5 µM of pNaKtide for 24 hours. The number of BrdU positive cells were then counted as an indication of cell proliferation.

Cell Culture.

Normal human primary retinal endothelial cells (HRMECs) were purchased from Cell Systems, WA. They were maintained in endothelial basal medium (EBM) containing growth factors and supplemented with 5% fetal bovine serum (FBS), prepared according to the manufacturer's protocol (referred hereafter as EGM-2 complete media). The EBM medium and supplements were purchased from Lonza (Basel, Switzerland). All experiments using HRMECs were performed between passages 3-8. During experiments, HRMECs were incubated in EGM-2 reduced media (referred hereafter as EGM-R media), which was comprised of EBM media containing ¼ the concentration of growth factors and 0.5% FBS.

BrdU Assay.

Bromodeoxyuridine (BrdU) is a thymidine nucleotide analog that is incorporated (instead of thymidine) during S-phase only in the DNA of proliferating cells. HRMECs were plated in 8-well collagen coated chamber slides at a density of 10,000 cells/well.

After overnight incubation at 37° C., the media was changed to EGM-R media. The cells were treated with the indicated concentrations of the peptides in EGMR for 24 hours at 37° C. The rate of BrdU incorporation was measured by the BrdU kit (Roche Biochemicals, Indianaplis, Ind., USA), according to manufacturer's instructions. The number of BrdU positive cells was counted in three independent fields per sample. The fraction of BrdU positive cells in the control untreated cells was assumed to be 1. The relative number of BrdU positive cells in the peptide-treated HRMECs was calculated as a fraction of the BrdU-incorporated HRMECs. Each sample was tested in duplicate, and the BrdU assay was performed 3 independent times.

All data were plotted using GraphPad Prism Software, Inc. (La Jolla, Calif., USA), and was represented as the mean±standard error of the mean (SEM). Results from the control and treated samples were compared using an analysis of variance followed by a Neumann-Keuls multiple comparison test. All analyses were completed using a 95% confidence interval. Data was considered significant when $p<0.05$.

Effect of pNaKtide on Angiogenesis and VEGF Expression.

To measure the effect of increase pNaKtide on HRMECs, cells were treated to promote differentiation of the cells into capillary tube-like structures. Cells were subsequently harvested, seeded on polymerized matrigel and supplemented with 0.5 µM, 1 µM, and 5 µM of pNaKtide and incubated for 24 hours. Further investigation of the effect of pNaKtide on angiogenesis and VEGF expression was performed in tumor xenograft models as described herein.

Matrigel Assay.

Growth Factor Reduced (GFR)-Matrigel (BD Biosciences, Bedford, Mass.) was used to promote the differentiation of HRMECs' into capillary tube-like structures. A total of 100 µL of thawed GFR-Matrigel was added to 96-well tissue culture plates, followed by incubation at 37° C. for 60 min to allow polymerization. Prior to the Matrigel assays, HRMECs were cultured in EGM-2 complete media to 70% confluence in 100 mm tissue culture dishes. On the day of the assay, HRMEC's were harvested and re-suspended in EGM-R medium. Subsequently the HRMECs ($2.0 \times 10^5$ cells/ml) were seeded on the polymerized GFR-Matrigel in EGM-R media, supplemented with the indicated concentrations of pNaKtide and were incubated for 24 hours at 37° C.

Angiogenic capillary tube formation was photographed using a Leica DMIL phase contrast microscope (Leica Microsystems, Welzar, Germany) in three independent fields per sample. Each sample was tested in duplicate and the entire experiment was performed 3 independent times.

Inhibition of Angiogenesis in Tumor Xenografts.

Tumor xenografts were established by subcutaneous injection of $5 \times 10^6$ DU145 cells into the left and right flanks for 6-week-old female NOD SCID mice (Charles River). When tumors reaches an average volume of 100 mm$^3$, mice were injected intraperitoneally (IP) with saline or pNaKtide (at doses of 2 mg/kg and 10 mg/kg body weight) every other day for five times. Tumors from control and pNaKtide-treated mice were analyzed for the ability of pNaKtide to inhibit in vivo angiogenesis. The tumors were immunostained with an antibody against CD-31 to identify vessels. A goat polyclonal anti-CD31 antibody and ImmPRESS Reagent anti-goat Ig peroxidase were used. Negative controls were performed by replacing primary antibody with normal goat immunoglobulins. Then, the CD-31 positive regions were quantified using Image J, and vascularity density was calculated as the percent of tumor tissue area occupied by vessels. The production of VEGF was also evaluated by Western blotting using anti-VEGF antibody.

Example 1—The pNaKtide Decreases the Proliferation of HRMEC in a Dose Dependent Manner The investigation of the effect of pNaKtide on the proliferation of mice HRMECs showed pNaKtide was effective in decreasing the proliferation of HRMECs. Effect of the test peptides on the proliferation of human retinal microvascular endothelial cells (HRMECs) over 24 hours shows the control peptide CBM-FF had no antiproliferative activity in HRMECs (FIG. 1). However, the pNaKtide peptide potently suppressed the proliferation of HRMECs at 0.5, 1 and 5 micromolar concentrations in a dose dependent manner (FIG. 1).

Figure 2A:
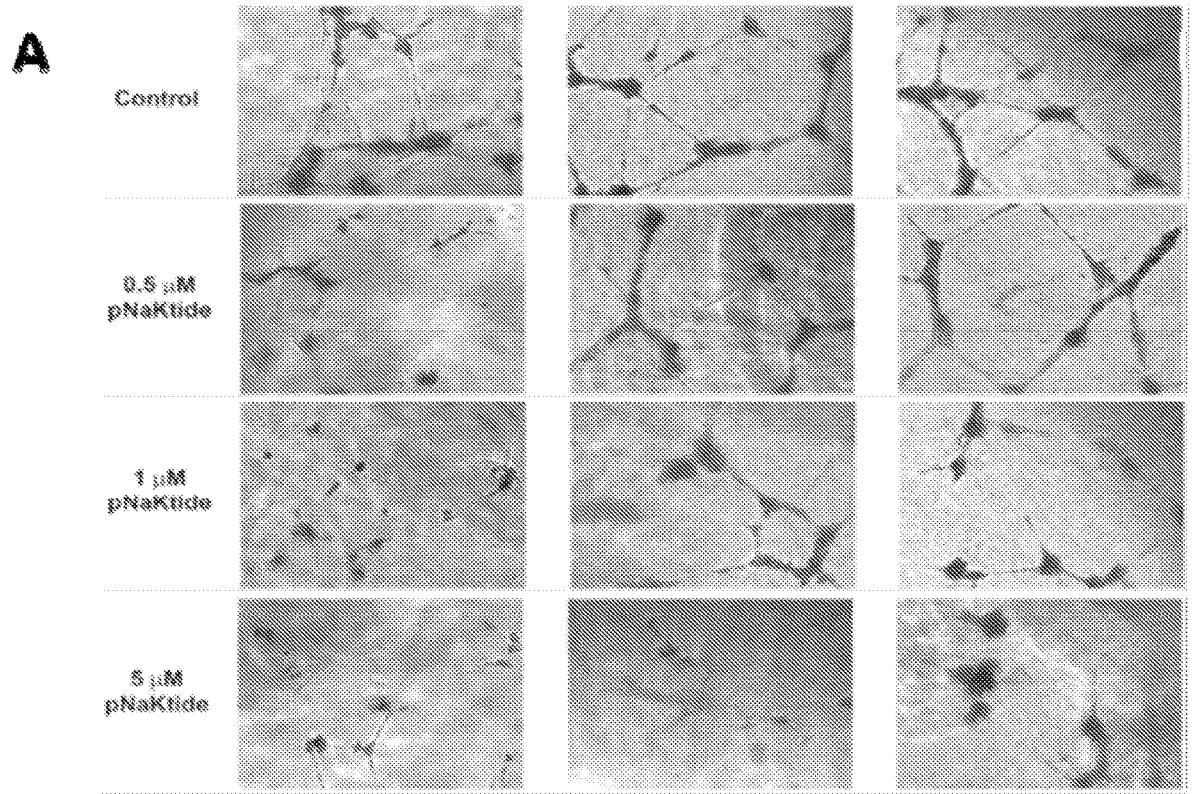
FIGS. 2A-2B include images and graphs showing the effect of increasing pNaKtide concentrations on angiogenesis in mouse HRMECs. The control panel (topmost panel) in FIG. 2A shows that HRMEC's form a robust network of angiogenic tubules on Matrigel. The bottom three panels show the results of increasing pNaKtide on angiogenic sprouting of HRMECs, with each panel showing three representative pictures from each of the samples.
Figure 2B:
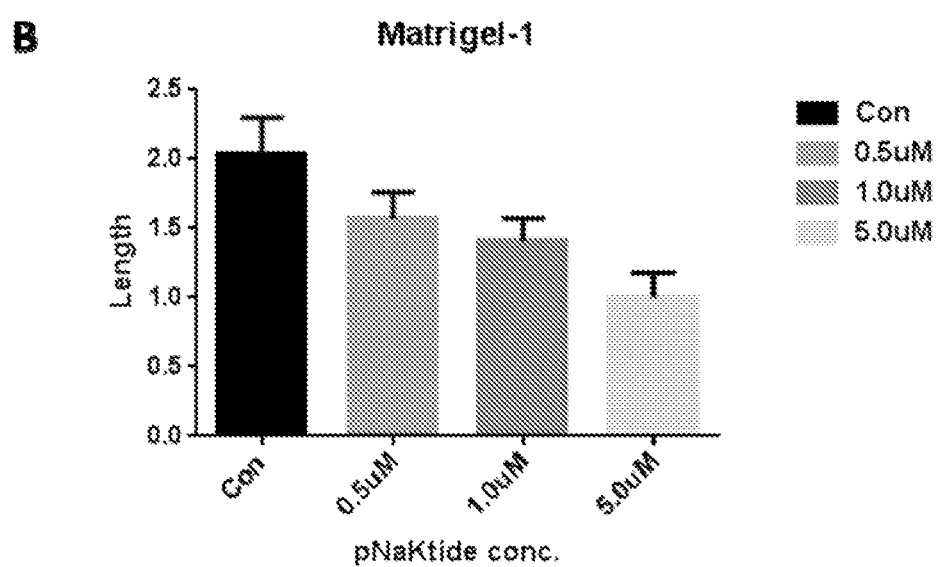

Example 2—The pNaKtide Decreases the Formation of Angiogenic Tubules in a Matrigel Assay Investigation of the formation of angiogenic tubules in mouse HRMECs was utilized to explore the effect of pNaKtide on angiogenesis. The control panel (topmost panel) in FIG. 2A shows that HRMEC's form a robust network of angiogenic tubules on Matrigel. When the pNaKtide peptide was present, there was a decrease in angiogenic sprouting of HRMECs as observed in the bottom three panels. The anti-angiogenic activity of pNaKtide was concentration dependent; the maximal effect being observed at 5 micromolar concentration of pNaKtide (FIG. 2B).

Figure 3A:
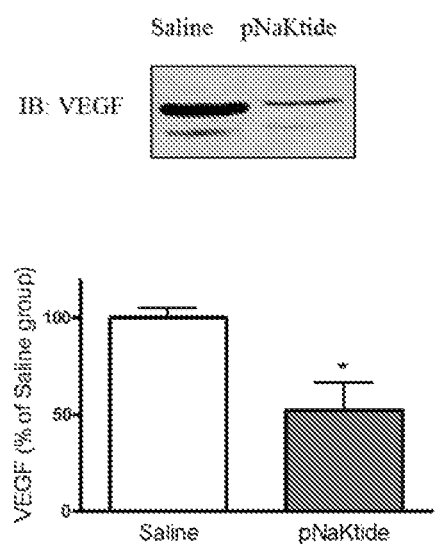
FIGS. 3A-3B include graphs and images showing the effect of pNaKtide treatment on VEGF expression and blood vessel formation in a mouse tumor xenograft model. pNaKtide treatment was administered at 2 or 10 mg/kg every two days, intraperitoneally.

Example 3—Effects of pNaKtide Treatment on VEGF Expression and Neovascularization In order to examine the effect of pNaKtide on VEGF expression and neovascularization, and probe whether application of pNaKtide was effective in blocking VEGF expression and angiogenesis, a tumor xenograft model was used, and blood vessel formation and VEGF expression were measured in tumors isolated from control and pNaKtide-treated animals. The results of expression of VEGF in tumor homogenates and the reduced VEGF expression in pNaKtide treated tumor homogenates are shown in FIG. 3A. The Western blot shows pNaKtide treatment produced a greater than 50% reduction in total VEGF.

Figure 3B:
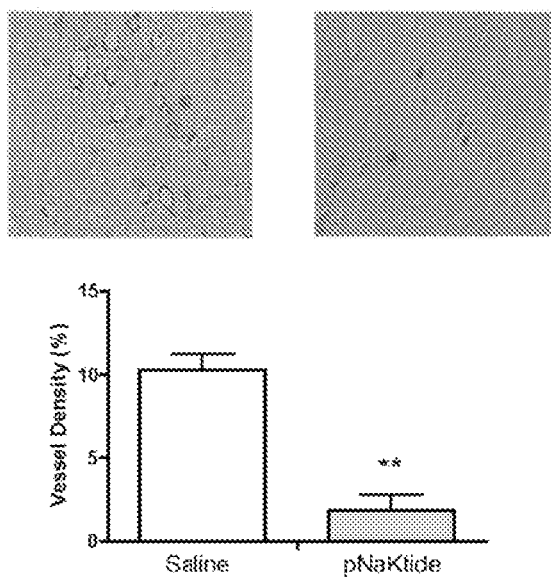
Figure 4:
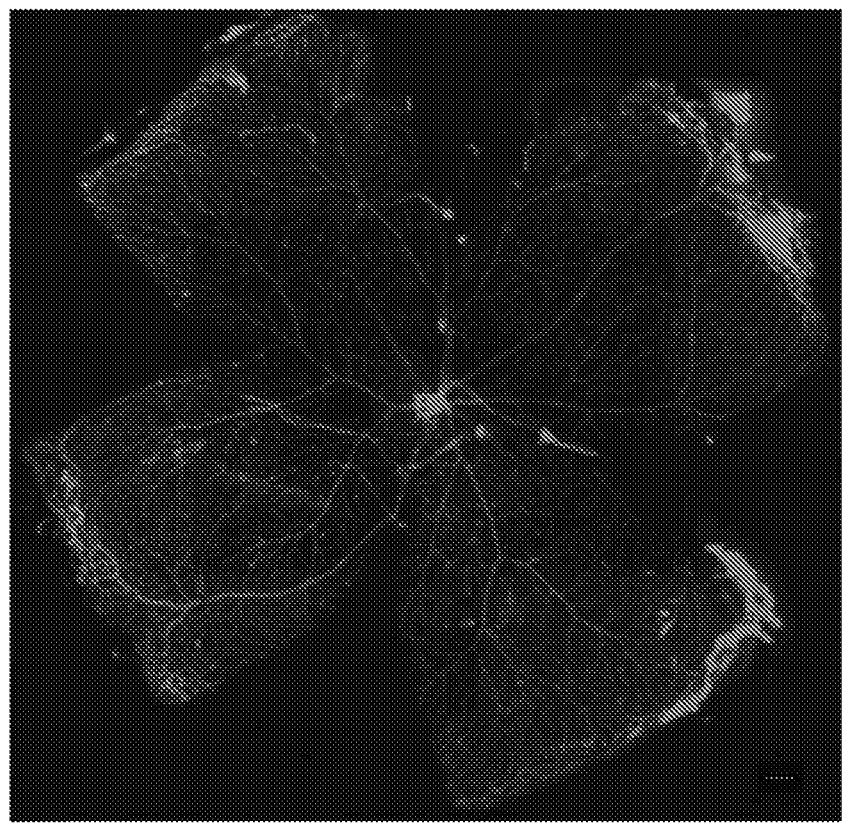
FIGS. 4-8 includes images of a retinal vasculature and graphs showing the effects of pNaKtide on neovascularization in a mouse model of oxygen-induced retinopathy (OIR).

The results of the investigation of effects of pNaKtide on angiogenesis show vessel density of xenograft tumors was reduced by pNaKtide treatment. The IHC staining of CD31 in the formalin-fixed, paraffin-embedded xenograft tumors (14 in saline group and 6 in 10 mg/kg pNaKtide group) is shown in FIG. 3B. The vessel density was calculated as the percent of tumor area occupied by vessels. The vessel density in control mice was approximately 10%, and pNaKtide treatment reduced the density to approximately 2.5%, as shown in the graph in FIG. 3B.

As shown in FIGS. 3A-3B, pNaKtide treatment (2 and 10 mg/kg every two days, i.p.) reduced VEGF expression and blood vessel formation. At 10 mg/kg, it inhibited about 50% of VEGF expression, resulting in a 70% reduction in new blood vessel formation. Taken together, the in vivo results thus indicated that administration of the pNaKtide was useful for inhibiting VEGF. Without wishing to be bound by any particular theory, because anti-VEGF therapy is clinically effective in diabetic retinopathy, it was believed that the blocking effect of pNaKtide on VEGF production would produce the same level of benefits as observed with anti-VEGF therapy.

Example 4—Effects of pNaKtide on Neovascularization

The effects of pNaKtide on neovascularization were also assessed in a mouse model of oxygen-induced retinopathy (OIR) according to the protocol developed in the laboratory of Smith. Briefly, litters of mice pups at postnatal day (P) 7 (C57BL/6, n=9) with their mothers were exposed in a chamber (BioSpherix Proox Model 110 Hyperoxia, BioSpherix, Ltd.) to high oxygen concentrations (75%±2%) for 5 days. At P12, mice were anesthetized by intraperitoneal injection of ketamine and xylazine mixture. pNaKtide was then dissolved in PBS at 0.25 µg/µl, and intravitreal injections were performed using a microsyringe (NanoFil syringe; World Precision Instruments, Inc., Sarasota, Fla., USA). pNaKtide (1 µl) was injected into the right eye, while the left eye was served as a control. Mice were killed at P17. The eyes were harvested immediately and fixed in 4% PFA for 1 h at room temperature. The retinae were dissected under a dissection microscope and stained with lectin solution that specifically binds to endothelial cells (Isolectin B4-594, Alexa Fluor 594-I21413, Molecular Probes). Under a dissection microscope, the stained retinae were cut four incisions and flat mounted.

Figure 5:
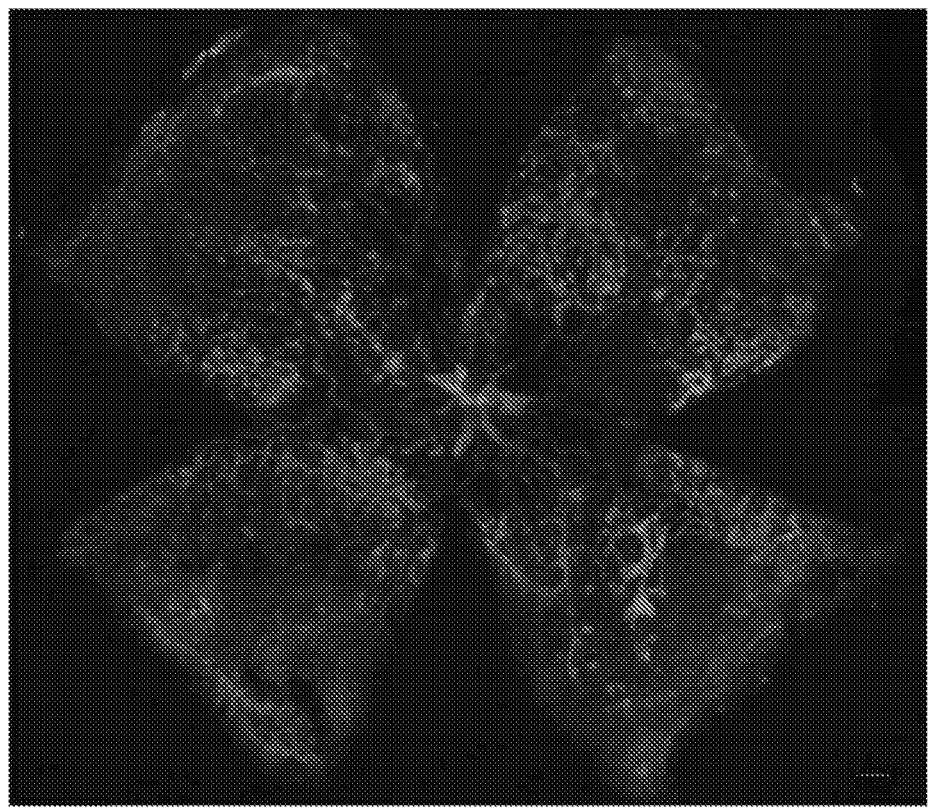
Figure 6:
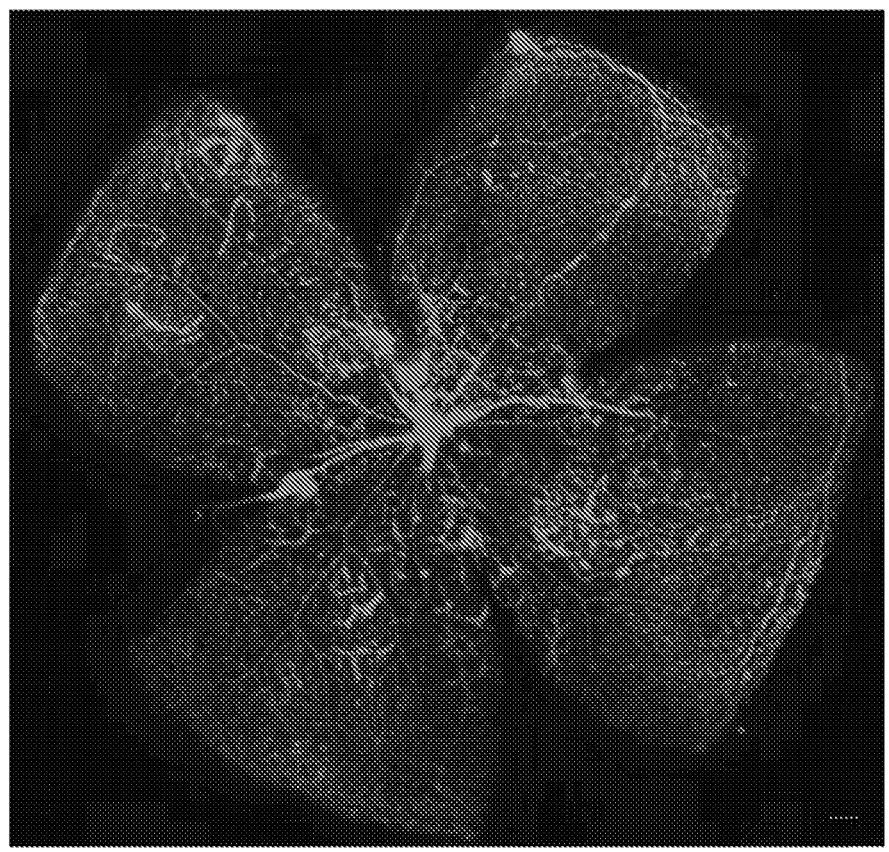
Figure 7:
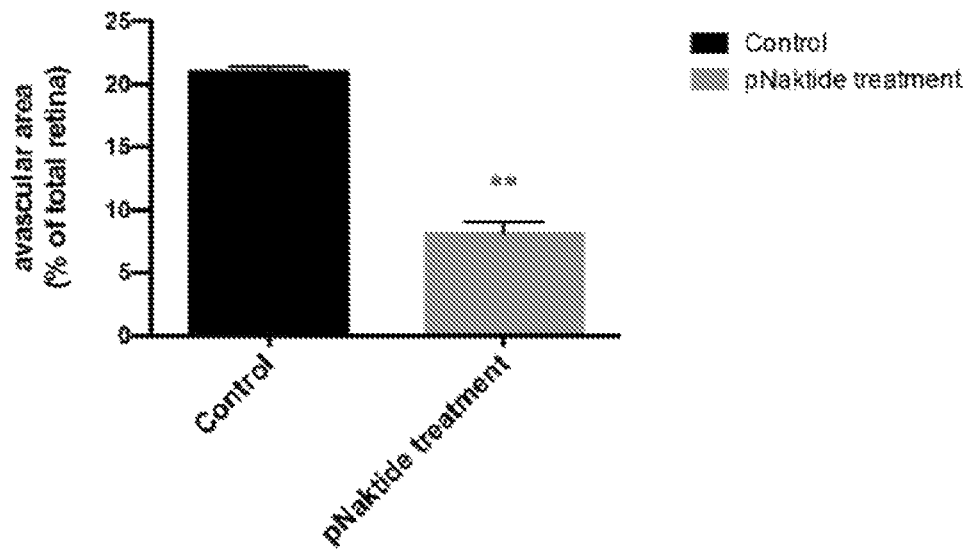
Figure 8:
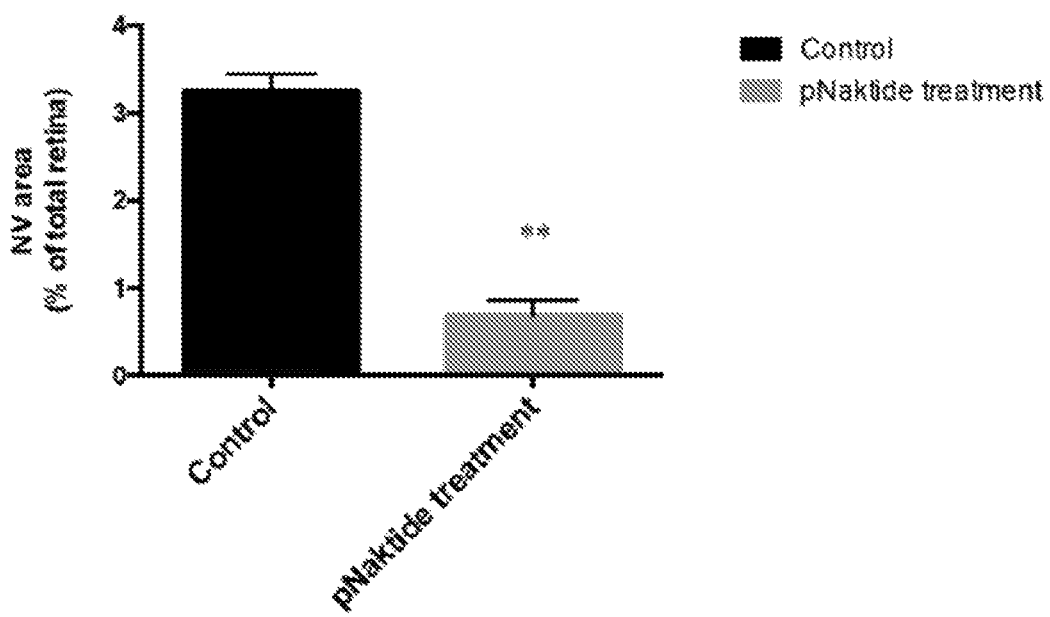

Images of the retinal vasculature were then obtained with Zeiss fluorescent microscope and then multiple images from the same retinae were analyzed for vascular loss and neovascularization using Photoshop and Image J software. As shown in the image of FIG. 6, intravitreous injection of pNaKtide decreased the amount of neovascularization, as compared to FIG. 5, the OIR control. These images show pNaKtide is potent and effective in blocking angiogenesis by inhibiting VEGF expression. FIGS. 7 and 8 show the quantification of the retinal vaso-obliteration and neovascular area of the retina as a percent of total retina, respectively. pNaKtide treatment reduced both the neovascular and retinal vaso-obliteration area of the total retina versus control treatment, which further confirmed that administration of pNaKtide was useful in the treatment of retinopathy.

Summary of Examples 1-4

The foregoing examples demonstrated that pNaKtide decreased cell proliferation in normal human primary retinal endothelial cells (HRMECs), and that inhibition of cell proliferation was dose-dependent. Moreover, when cells were grown in matrigels, pNaKtide dose-dependently reduced angiogenic capillary tube formation. The examples further showed that pNaKtide inhibits VEGF expression and blood vessel formation, and is potent and effective in blocking angiogenesis, particularly in retinal vasculature.

It will be understood that various details of the presently disclosed subject matter can be changed without departing from the scope of the subject matter disclosed herein. Furthermore, the description provided herein is for the purpose of illustration only, and not for the purpose of limitation.

Additionally, while the terms used herein are believed to be well understood by one of ordinary skill in the art, definitions are set forth to facilitate explanation of the presently-disclosed subject matter. Unless defined otherwise, all technical and scientific terms used herein have the same meaning as commonly understood by one of ordinary skill in the art to which the presently-disclosed subject matter belongs. Although many methods, devices, and materials similar or equivalent to those described herein can be used in the practice or testing of the presently-disclosed subject matter, representative methods, devices, and materials are now described.

Furthermore, following long-standing patent law convention, the terms "a", "an", and "the" refer to "one or more" when used in this application, including the claims. Thus, for example, reference to "a polypeptide" includes a plurality of such polypeptide, and so forth. Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations in some embodiments of ±20%, in some embodiments of ±10%, in some embodiments of ±5%, in some embodiments of ±1%, in some embodiments of ±0.5%, and in some embodiments of ±0.1% from the specified amount, as such variations are appropriate to perform the disclosed method. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

Throughout this document, various references are mentioned. All such references are incorporated herein by reference, including the references set forth in the following list:

REFERENCES

1. International Patent Application Publication No. WO 2008/054792, of Xie, entitled "Na/K-ATPase-Specific Peptide Inhibitors/Activators of Src and Src Family Kinases."
2. International Patent Application Publication No. WO 2010/071767, of Xie, entitled "Na/K-ATPase-Derived Src Inhibitors and Ouabain Antagonists and Uses Thereof."
3. Wang, et al. "Involvement of Na/K-ATPase in hydrogen peroxide-induced activation of the Src/ERK pathway in LLC-PK1 cells." Free Radical Biology and Medicine. 2014, 71: 415-426.
4. Yan, et al. "Involvement of Reactive Oxygen Species in a Feed-forward Mechanism of Na/K-ATPase-mediated Signaling Transduction." Journal of Biological Chemistry. 2013, 288: 34249-34258.
5. Wild, S., et al., Global prevalence of diabetes: estimates for the year 2000 and projections for 2030. Diabetes Care, 2004. 27(5): p. 1047-53.
6. Klein, R., et al., The Wisconsin Epidemiologic Study of Diabetic Retinopathy: XVII. The 14-year incidence and progression of diabetic retinopathy and associated risk factors in type 1 diabetes. Ophthalmology, 1998. 105(10): p. 1801-15.
7. Klein, R., B. E. Klein, and S. E. Moss, *The Wisconsin epidemiological study of diabetic retinopathy: a review.* Diabetes Metab Rev, 1989. 5(7): p. 559-70.
8. Kempen, J. H., et al., The prevalence of diabetic retinopathy among adults in the United States. Arch Ophthalmol, 2004. 122(4): p. 552-63.
9. Antonetti, D. A., R. Klein, and T. W. Gardner, *Diabetic retinopathy.* N Engl J Med, 2012. 366(13): p. 1227-39.
10. Preliminary report on effects of photocoagulation therapy. The Diabetic Retinopathy Study Research Group. Am J Ophthalmol, 1976. 81(4): p. 383-96.
11. Early Treatment Diabetic Retinopathy Study design and baseline patient characteristics. ETDRS report number 7. Ophthalmology, 1991. 98(5 Suppl): p. 741-56.
12. Cheung, N., P. Mitchell, and T. Y. Wong, *Diabetic retinopathy.* Lancet, 2010. 376(9735): p. 124-36.
13. Senger, D. R., et al., Tumor cells secrete a vascular permeability factor that promotes accumulation of ascites fluid. Science, 1983. 219(4587): p. 983-5.
14. Murata, T., et al., Vascular endothelial growth factor plays a role in hyperpermeability of diabetic retinal vessels. Ophthalmic Res, 1995. 27(1): p. 48-52.
15. Leung, D. W., et al., Vascular endothelial growth factor is a secreted angiogenic mitogen. Science, 1989. 246 (4935): p. 1306-9.
16. Adamis, A. P., et al., Increased vascular endothelial growth factor levels in the vitreous of eyes with proliferative diabetic retinopathy. Am J Ophthalmol, 1994. 118(4): p. 445-50.
17. Aiello, L. P., et al., Vascular endothelial growth factor in ocular fluid of patients with diabetic retinopathy and other retinal disorders. N Engl J Med, 1994. 331(22): p. 1480-7.

18. Tolentino, M. J., et al., Intravitreous injections of vascular endothelial growth factor produce retinal ischemia and microangiopathy in an adult primate. Ophthalmology, 1996. 103(11): p. 1820-8.
19. Tolentino, M. J., et al., Pathologic features of vascular endothelial growth factor-induced retinopathy in the non-human primate. Am J Ophthalmol, 2002. 133(3): p. 373-85.
20. Arevalo, J. F., et al., Intravitreal Bevacizumab (Avastin) for Diabetic Retinopathy: The 2010 GLADAOF Lecture. J Ophthalmol, 2011. 2011: p. 584238.
21. Ferrara, N., et al., Discovery and development of bevacizumab, an anti-VEGF antibody for treating cancer. Nat Rev Drug Discov, 2004. 3(5): p. 391-400.
22. Arevalo, J. F., et al., Primary intravitreal bevacizumab (Avastin) for diabetic macular edema: results from the Pan-American Collaborative Retina Study Group at 6-month follow-up. Ophthalmology, 2007. 114(4): p. 743-50.
23. Bhaysar, A. R., et al., Evaluation of results 1 year following short-term use of ranibizumab for vitreous hemorrhage due to proliferative diabetic retinopathy. JAMA Ophthalmol, 2014. 132(7): p. 889-90.
24. Randomized clinical trial evaluating intravitreal ranibizumab or saline for vitreous hemorrhage from proliferative diabetic retinopathy. JAMA Ophthalmol, 2013. 131(3): p. 283-93.
25. Wirostko, B., T. Y. Wong, and R. Simo, *Vascular endothelial growth factor and diabetic complications*. Prog Retin Eye Res, 2008. 27(6): p. 608-21.
26. Agard, E., et al., Repeated intravitreal anti-vascular endothelial growth factor injections can induce iatrogenic ocular hypertension, especially in patients with open-angle glaucoma. Can J Ophthalmol, 2015. 50(2): p. 127-31.
27. SooHoo, J. R., L. K. Seibold, and M. Y. Kahook, *The link between intravitreal antivascular endothelial growth factor injections and glaucoma*. Curr Opin Ophthalmol, 2014. 25(2): p. 127-33.
28. Wong, T. Y., G. Liew, and P. Mitchell, *Clinical update: new treatments for age-related macular degeneration*. Lancet, 2007. 370(9583): p. 204-6.
29. Connor, K. M., N. M. Krah, R. J. Dennison, C. M. Aderman, J. Chen, K. I. Guerin, P. Sapieha, A. Stahl, K. L. Willett and L. E. Smith (2009). "Quantification of oxygen-induced retinopathy in the mouse: a model of vessel loss, vessel regrowth and pathological angiogenesis." Nat Protoc 4(11): 1565-1573.
30. Venkatesh, A., S. Ma, F. Langellotto, G. Gao and C. Punzo (2013). "Retinal gene delivery by rAAV and DNA electroporation." Curr Protoc Microbiol Chapter 14: Unit 14D.14.
31. Stahl, A., K. M. Connor, P. Sapieha, K. L. Willett, N. M. Krah, R. J. Dennison, J. Chen, K. I. Guerin and L. E. Smith (2009). "Computer-aided quantification of retinal neovascularization." Angiogenesis 12(3): 297-301.

| SEQUENCE LISTING |
| --- |
| SEQ ID NO: 1<br>SATWLALSRIAGLCNRAVFQ |
| SEQ ID NO: 2<br>GRKKRRQRRRPPQ |
| SEQ ID NO: 3<br>RQIKIWFQNRRNIKWKK |
| SEQ ID NO: 4<br>KKGKKGKK |
| SEQ ID NO: 5<br>GRKKRRQRRRPPQSATWLALSRIAGLCNRAVFQ |

What is claimed is:

1. A method for treating retinopathy, comprising administering an effective amount of polypeptide antagonist of a Na/K ATPase/Src receptor complex to a subject in need thereof, wherein the polypeptide antagonist comprises the sequence of SEQ ID NO: 1, or a fragment thereof.

2. The method of claim 1, wherein the polypeptide antagonist further includes a cell penetrating polypeptide selected from the group consisting of SEQ ID NOS: 2-4.

3. The method of claim 1, wherein the retinopathy is diabetic retinopathy.

4. The method of claim 1, wherein the administering step includes intravitreous administration, subconjunctival administration, intracameral administration, intraocular administration, or combinations thereof.

5. The method of claim 1, wherein administering the polypeptide antagonist decreases cell proliferation in an eye of a subject.

6. The method of claim 1, wherein administering the polypeptide antagonist decreases VEGF expression, angiogenesis, and/or capillary tube formation in an eye of a subject.

7. The method of claim 1, wherein administering the polypeptide antagonist decreases neovascularization in an eye of a subject.

8. A method of decreasing angiogenesis in a retinal vasculature, comprising administering a polypeptide antagonist of a Na/K ATPase/Src receptor complex to a subject in need thereof, wherein the polypeptide antagonist comprises the sequence of SEQ ID NO: 1, or a fragment thereof.

9. The method of claim 8, wherein the polypeptide antagonist further includes a cell penetrating polypeptide selected from the group consisting of SEQ ID NOS: 2-4 .

10. The method of claim 8, wherein administering the polypeptide antagonist comprises intravitreous injection of the polypeptide antagonist.

* * * * *